United States Patent [19]

Berke et al.

[11] 4,340,060
[45] Jul. 20, 1982

[54] FLEXIBLE CRANIOTOME FOOTPLATE

[75] Inventors: Joseph J. Berke, 3333 E. Jefferson, Detroit, Mich. 48207; Eric L. Gay, Ann Arbor, Mich.

[73] Assignee: Joseph J. Berke, Detroit, Mich.

[21] Appl. No.: 159,481

[22] Filed: Jun. 16, 1980

[51] Int. Cl.³ ............................................. A61B 17/14
[52] U.S. Cl. ...................................... 128/317; 30/370
[58] Field of Search ................... 128/317, 305.1, 305, 128/92 E, 3, 310, 91 A; 30/370, 273, 275, 290; 83/925 CC

[56] References Cited
U.S. PATENT DOCUMENTS 2,492,156  12/1949  Kupjack ............................... 30/370
3,882,855  5/1975  Schulte et al. ........................ 128/20

Primary Examiner—Michael H. Thaler
Attorney, Agent, or Firm—Cullen, Sloman, Cantor, Grauer, Scott & Rutherford

[57] ABSTRACT

An improved craniotome footplate, or dura guard for cutting between bur holes or from a single bur hole in the skull without damaging the dura membrane which is intermediate the underside of the skull and the brain. The guard includes a flexible, resilient tip for negotiating bony prominences on the underside of the skull and for separating the dura from the underside of the skull in advance of the craniotome cutting of the skull.

5 Claims, 11 Drawing Figures

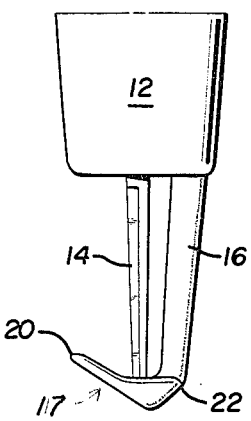
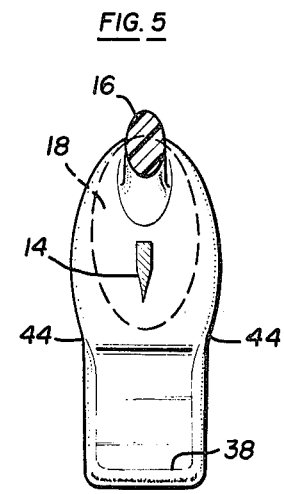
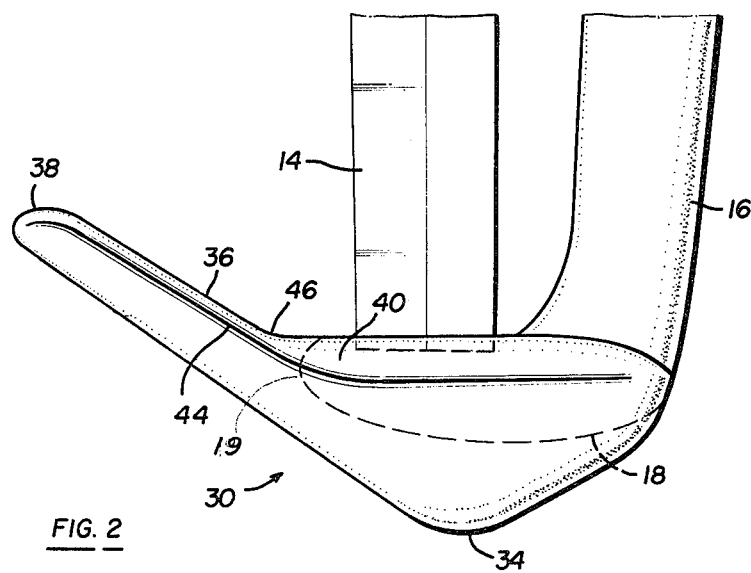
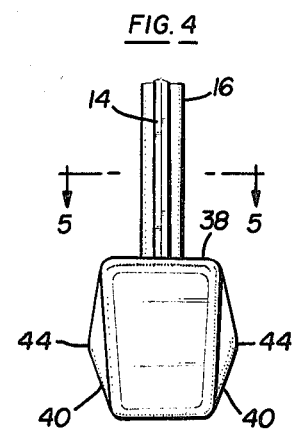
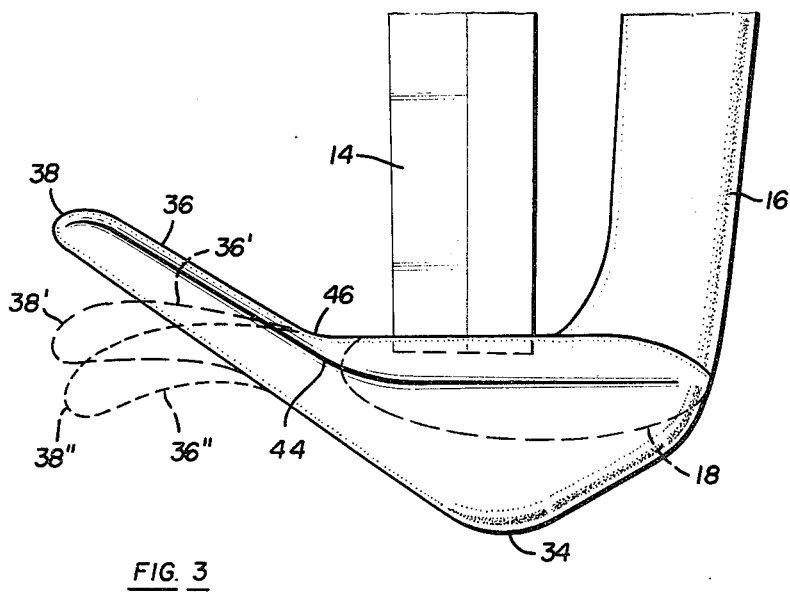
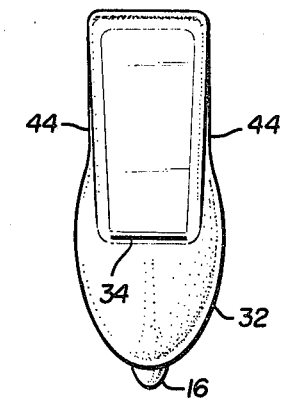
FIG. 1 PRIOR ART
FIG. 2
FIG. 3
FIG. 4
FIG. 5
FIG. 6

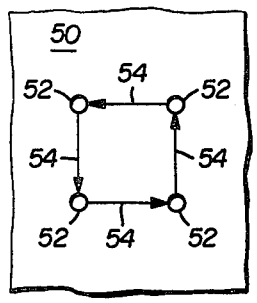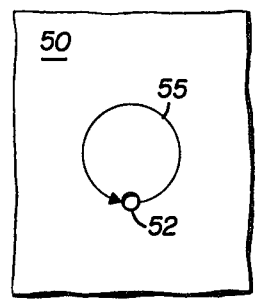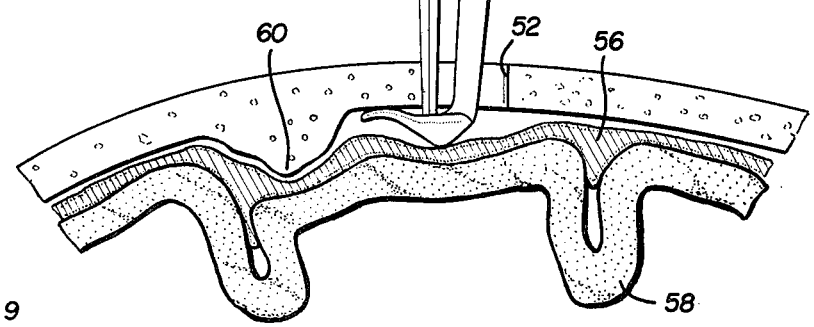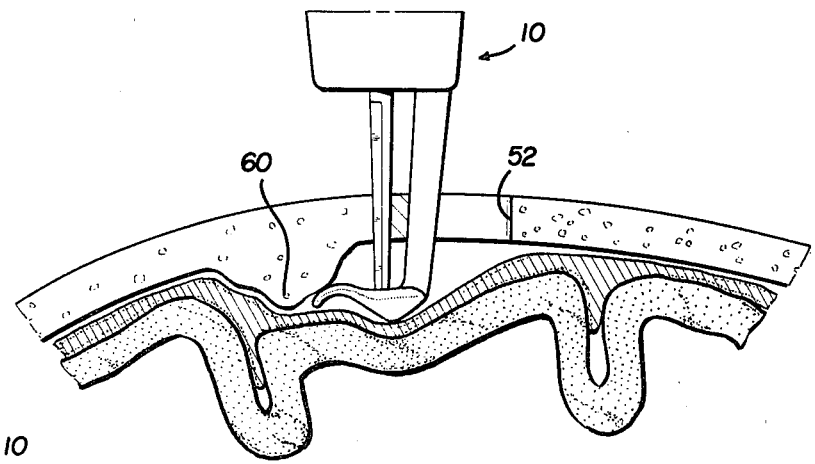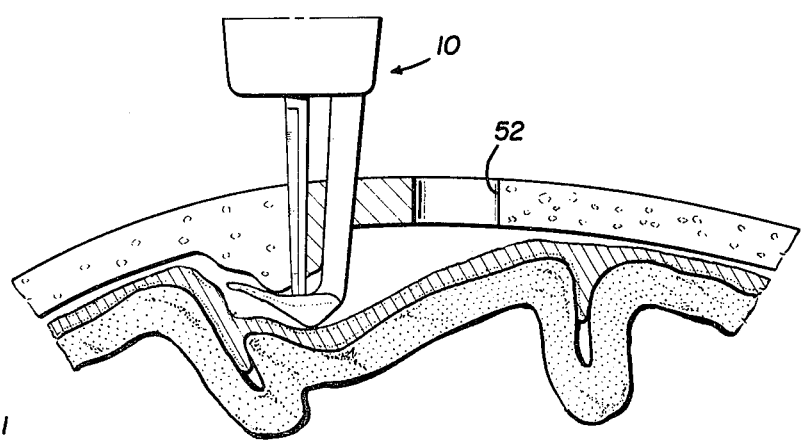

PLEXIBLE CRANIOTOME FOOTPLATE

BACKGROUND OF THE INVENTION

The present invention relates to improved surgical instruments and, more particularly, to an improvement to the craniotome. A craniotome is well known as a surgical instrument utilized in performing a craniotomy where a series of bur holes are first drilled in the skull and then a craniotome is used to cut between bur holes. After several bur holes have been cut and the craniotome utilized to cut between adjacent bur holes, a section of the skull may thus be removed.

It is well known that there are a series of three meninges or membranes which cover the brain, the outermost of which is the dura mater, commonly referred to as the dura. The dura is thus positioned between the brain and the underside of the skull itself. When performing a craniotomy it is desirable to avoid tearing, cutting or rupturing the dura. However, the dura tends to adhere to the underside of the skull and this adherence becomes more pronounced in more elderly subjects. Furthermore the dura is more fibrous with increasing age and thus easier to tear with tool movement.

Prior to the present invention the safest technique for stripping or removing the dura was laborious, tedious, and painstakingly slow. After first drilling bur holes, the procedure includes inserting a long, thin spatula through a bur hole to strip a portion of the dura from the underside of the skull between two bur holes. Then the surgeon removed the spatula, and inserted a craniotome and cut the skull between these two bur holes, then removed the craniotome and re-inserted the spatula to strip the dura from the underside of the skull between the next pair of bur holes. Thereafter, the craniotome was re-inserted, an additional cut was made, the craniotome removed, the spatula re-inserted, and additional dura stripped from the underside of the skull. Thus it may be appreciated that only a short segment of the dura could be stripped at a time and thereafter a corresponding short segment of the skull could be cut by the craniotome.

Furthermore, when negotiating a bony prominence of the skull, it was always difficult to strip the dura from the far or distant side of the bony prominence. Various forms of craniotomes have been developed including those with a rigid metal foot. One function of the metal foot is to strip the dura from the underside of the skull and even a rigid swiveling foot has been proposed. However, the rigid metal foot can not negotiate a bony prominence and thus present a significant risk to the patient.

The present invention marks a significant departure from the prior technique and provides an improved craniotome which permits continuous cutting of the skull between bur holes or from a single bur hole, and automatically strips the dura from the underside of the skull. Thus there is no need to remove the craniotome repeatedly and insert a separate instrument such as a spatula. Thus the surgical procedure for removing the skull portion is safer and may be performed more quickly. Also, the use of fewer, smaller bur holes is possible with the present invention thus reducing the amount of bone which is drilled away and hence non-replaceable, thus promoting more rapid healing and reducing disfigurement of the skull.

SUMMARY OF THE INVENTION

The present invention provides an improvement for a craniotome which permits the craniotome to cut the skull continuously and automatically strips the dura, on a continuous basis, in the region where the craniotome is about to cut. The craniotome includes, as is conventional, a handle, a support column which extends vertically downwardly from the handle and terminates in a horizontal support foot, and a cutting element or blade which extends from the handle downwardly, substantially parallel to the support column, and terminates at the support foot. The present invention includes a flexible footplate on the craniotome support foot which extends forwardly of the support foot. The footplate is flexible and resilient and thus follows the contour of the underside of the skull and separates or strips the dura mater from the underside of the skull, with no requirement for altering the common practices of craniotome motion, attitude relative to the skull surface, or upward force during cutting.

BRIEF DESCRIPTION OF THE DRAWINGS

The various benefits and advantages of the present invention will be more fully understood upon reading the detailed description of the invention taken in conjunction with the drawings. In the drawings, wherein like reference numerals identify corresponding components:

FIG. 1 is a partial side elevation view of a conventional form of craniotome;

FIG. 2 is an enlarged partial side elevation view of a craniotome including the flexible footplate of the present invention;

FIG. 3 is an enlarged partial side elevation view of the craniotome of FIG. 2 demonstrating the various positions of the flexible footplate during use;

FIG. 4 is a partial front elevation view of the craniotome footplate of the present invention;

FIG. 5 is a plan view of a craniotome including a flexible footplate of the present invention as seen in the plane 5—5 of FIG. 4;

FIG. 6 is a bottom elevational view of the flexible footplate of the present invention;

FIGS. 7 and 8 are diagrammatic plan views of the skull illustrating the location of bur holes as part of the craniotomy procedure; and FIGS. 9, 10 and 11 are sectional side views illustrating the use of the present invention in stripping the dura from the underside of the skull.

DETAILED DESCRIPTION OF THE INVENTION

Referring to the drawings and particularly FIG. 1, there is illustrated a conventional craniotome 10 having a handle 12. Extending downwardly from the handle 12 is a vertically reciprocable cutting blade 14. Also extending downwardly from the handle 12 is a vertical support column 16 which extends generally parallel to the blade 14 and terminates in a right angled or horizontal foot 17. The foot 17 has a forward end 20 which is positioned away from the support column 16 and a rear portion or heel 22 which is the juncture of the horizontal portions. The forward portion 20 of the foot 17 is considered the leading edge and the rear portion 22 of the foot is considered the trailing edge. The terms "forward" and "rearward" are used in the context of the direction of movement of the craniotome during surgery. The foot 17 also provides a bearing surface for the end of the blade 14, the bearing surface being intermediate the leading and trailing ends of the foot 17. As is conventional, the blade, support and foot are made of steel.

With reference to FIGS. 2 through 6 there is illustrated, in partial elevation view, the improved craniotome of the present invention including the flexible elastic footplate 30. The flexible, elastic footplate 30, which is preferably cast in place over the foot 18 of the craniotome, has a trailing or rear portion 32 which covers the trailing edge 22 of the foot 18. The footplate extends forwardly and downwardly from the trailing end 32 to a bottom portion 34 and then extends further forwardly and upwardly in a forward extension 36. The forward extension 36 extends beyond the leading edge 19 of the foot 18, and terminates in a forward tip 38. Thus the flexible, elastic footplate of the present invention is of a greater size, from leading edge to trailing edge, than the foot 18. The footplate 30 is also of a greater height, from top to bottom, than the height of the foot 18.

By way of example only, and not by way of limitation, the presently preferred material for the flexible footplate 30 is a polyester elastomer such as DuPont's Hytrel having a hardness of 55 durometer D, a tensile strength of 6400 psi, 500% elongation at break and a flexural modulus of 30,000 psi. This particular material satisfactorily retains sufficient tensile strength at temperatures in excess of the temperatures to which the craniotome is subjected by blade friction during surgery.

The dimensions of the flexible, elastomeric footplate, in the preferred embodiment are the overall height of 5 millimeters, and overall length of 8 to 9 millimeters, a side-to-side width of 5 millimeters at the widest point with the front or forward tip 38 being approximately 4 millimeters wide, side-to-side. As illustrated in FIGS. 2 through 6, the flexible footplate has convex sidewalls 40 with the widest part of the footplate 44, side-to-side, being intermediate the top 46 and bottom or heel 34 of the footplate. The importance of the tip width is to avoid snagging the tip on small surface details which may be present on the underside of the skull.

Referring next to FIG. 3 the various positions of the forward extension 36 and forward tip 38 of the flexible footplate 30 are illustrated. Specifically, in the free position, i.e., without any bearing or load, the forward tip 38 is approximately 5 millimeters above or higher than the bottom 34 of the footplate. In normal cutting when the forward tip 38 is stripping the dura from underneath the skull, the forward tip 38 will be subjected to a downward vertical force and the forward tip and forward extension will flex downward slightly, approximately 0.8 millimeters. When the flexible footplate negotiates a bony prominence under the skull, maximum flexing of the forward extension 36 and forward tip 38 will be experienced, this maximum flexing being approximately 1.5 millimeters. In FIG. 3, the free or unloaded position is illustrated in the solid line, the normal cutting position is illustrated with dashed lines and the forward tip is illustrated as 38', and the maximum anticipated deflection of 1.5 millimeters during cutting against bony prominences is illustrated in the dotted line with the forward extension and forward tip being illustrated as 36" and 38", respectively.

The tip 38 and the heel 34 cooperate to provide the proper stripping of the dura from the skull. Specifically, the narrower tip separates the dura from the skull while the wider portions of the footplate, including the heel, depress the dura transversely of the direction of movement of the craniotome to complete the stripping of the dura.

Referring now to FIG. 7 there is illustrated a top plan view of the skull 50 with a series of four bur holes 52 having been drilled in the skull as part of the craniotomy procedure. Thereafter, the craniotome is inserted in a bur hole and a cut is made, as illustrated by the arrow 54 to the next bur hole. This procedure is repeated from bur hole to bur hole until a portion of the skull may be removed.

Referring to FIG. 8, the present invention also permits some craniotomy procedures where only a single bur hole 52 is drilled as small as 1 cm in diameter, and the craniotome is inserted through the bur hole and moved in a complete circular path 55.

Referring next to FIGS. 9, 10 and 11, the use and benefits of the present invention will be more fully described.

In each of FIGS. 9, 10 and 11, it is to be assumed that the craniotome having the flexible elastic footplate of the present invention is moving from right to left during the cutting. FIG. 9 illustrates the craniotome which has been inserted through a bur hole 52 such that the flexible footplate 30 is positioned between the underside of the skull and the dura 56. As illustrated, the dura 56 is positioned between the underside of the skull 50 and the brain 58. The forward extension 36 and forward tip 38 of the flexible elastic footplate 30 are illustrated as being in the normal cutting position, i.e., there is some flexure because of the normal upward force applied to the craniotome to assure contact between the footplate and the underside of the skull.

FIG. 10 illustrates the footplate after further cutting of the skull by the craniotome. The forward tip 38 of the flexible footplate 30 is deformed or flexed because of the bony prominence 60 on the underside of the skull. This extreme deformation or flexing of the forward extension and forward tip of the footplate strips the dura off the bony prominence 60 to avoid tearing the dura as the craniotome continues to cut through the skull.

FIG. 11 illustrates the flexible footplate after completion of negotiating the bony prominence 60 with the forward extension 36 and forward tip 38 of the footplate returning to a normal cutting angle.

During surgical testing and evaluation of the present invention, including a surgical procedure involving an older patient having a more fibrous and more adherent dura, it was determined that the present invention operated as contemplated in that the flexible footplate maintained solid contact with the underside of the skull, the flexing movement of the forward extension and forward tip of the footplate did not affect movement or use of the craniotome adversely and there was no apparent tearing of the dura mater membrane. The normal heating of the craniotome during use had no apparent effect upon the elastomeric properties of the flexible footplate.

The present flexible footplate may be cast on a stationary foot craniotome or on a swivelling foot craniotome, although the optimum use of the flexible footplate is on a swivelling foot craniotome. Craniotomes having a rigid steel foot, both stationary and swivelling, are of course well-known. It is also contemplated, subject to testing, that the flexible footplate of the present invention will permit use of a craniotome to cut across the sagittal sinus without the need for the manual procedure using a spatula, as previously described.

Having thus described the present invention, it should be appreciated that various changes and modifications may be made without departing from the spirit and scope of the present invention. The invention, therefore, should be limited only by the scope of the following claims.

What is claimed is:

1. In combination with a craniotome having a handle, a downwardly depending blade, a support member extending downwardly from said handle substantially parallel to the blade, said support member terminating in a support foot generally perpendicular to the longitudinal axis of the blade, said blade bearing on said support foot intermediate the ends of said support foot, the improvement comprising:

a flexible, elastomeric extension on said support foot, said elastomeric extension including a downwardly extending heel portion on the part of the support foot opposite to where the blade bears on said support foot;

said flexible elastomeric extension further including a tip portion which extends forwardly and away from one end of said support foot opposite to where said support member terminates;

said forwardly extending flexible elastomeric tip being essentially free of non-flexible material;

such that upon normal use of the craniotome the tip flexes to negotiate bony prominences and also separates the dura from the underside of the skull and the downwardly extending heel depresses the dura to completely strip the dura from the skull.

2. The invention as defined in claim 1 wherein said flexible extension increases in width, side-to-side, from the tip toward the heel.

3. The invention as defined in claim 1 wherein said flexible extension increases in thickness, top-to-bottom, from the tip to the heel.

4. The invention as defined in claim 1 wherein said flexible extension includes opposed convex side walls.

5. The invention as defined in claim 1 wherein said downwardly extending heel depresses the dura in a direction transversely to the direction of normal forward craniotome movement.

* * * * *